United States Patent [19]

Pospisil et al.

[11] Patent Number: 5,692,896
[45] Date of Patent: Dec. 2, 1997

[54] LIGHT-TRANSMISSIVE ORTHODONTIC BRACKET WTH ALIGNMENT AND INDENTIFICATION MARKING

[75] Inventors: Jirina V. Pospisil, Covina; John S. Kelly, Arcadia; Joseph M. Caruso, Aguadulce, all of Calif.

[73] Assignee: Minnesota Mining And Manufacturing Co., St. Paul, Minn.

[21] Appl. No.: 404,369

[22] Filed: Mar. 15, 1995

[51] Int. Cl.$^6$ ..................... A61C 7/14
[52] U.S. Cl. ..................... 433/8; 206/369
[58] Field of Search ............ 433/3, 8, 9, 77; 206/63.5, 369, 534

[56] References Cited

U.S. PATENT DOCUMENTS

| | | | |
|---|---|---|---|
| 3,496,637 | 2/1970 | Etengoff | 433/9 |
| 4,050,156 | 9/1977 | Chasanoff et al. | 433/8 |
| 4,134,208 | 1/1979 | Pearlman | 433/8 |
| 4,279,593 | 7/1981 | Röhlcke | 433/8 |
| 4,299,569 | 11/1981 | Frantz | 433/8 |
| 4,302,532 | 11/1981 | Wallshein | 433/8 |
| 4,415,330 | 11/1983 | Daisley et al. | 433/16 |
| 4,551,096 | 11/1985 | Dellinger | 433/24 |
| 4,626,208 | 12/1986 | Hall | 433/3 |
| 4,639,218 | 1/1987 | Jones et al. | 433/8 |
| 4,819,316 | 4/1989 | Rossini et al. | 29/160.6 |
| 4,952,141 | 8/1990 | Wool | 433/8 |
| 4,954,080 | 9/1990 | Kelly et al. | 433/8 |
| 5,074,783 | 12/1991 | Reher | 433/8 |
| 5,096,417 | 3/1992 | Greenberg et al. | 433/24 |
| 5,221,202 | 6/1993 | James | 433/9 |
| 5,289,919 | 3/1994 | Fischer | 206/369 |
| 5,318,440 | 6/1994 | Adam et al. | 433/8 |
| 5,326,259 | 7/1994 | Rohlcke et al. | 433/8 |
| 5,348,154 | 9/1994 | Jacobs et al. | 206/369 |
| 5,350,059 | 9/1994 | Chester et al. | 206/63.5 |
| 5,354,199 | 10/1994 | Jacobs et al. | 433/9 |
| 5,358,402 | 10/1994 | Reed et al. | 433/8 |
| 5,380,196 | 1/1995 | Kelly et al. | 433/8 |
| 5,542,844 | 8/1996 | Perret, Jr. | 433/9 |

OTHER PUBLICATIONS

Mini–Twin Series Bracket Identification Charts, "A" Company 1993.
"Fascination" brochure, Dentaurum, May 1994.
Spirit™ Bonding Instructions, Ormco, no date.

*Primary Examiner*—Cary E. O'Connor
*Attorney, Agent, or Firm*—Gary L. Griswold; Walter N. Kirn; James D. Christoff

[57] ABSTRACT

Orthodontic brackets made of a light-transmissive material such as plastic or ceramic have a removable, water-based colorant to facilitate identification of the bracket and alignment of the bracket on the patient's tooth. The colorant is received in a ligature channel of the bracket and is visible through adjacent tiewings of the bracket. The colorant is protected by the overlying tiewings from inadvertent damage or removal as might otherwise occur during initial handling and placement of the bracket.

14 Claims, 1 Drawing Sheet

LIGHT-TRANSMISSIVE ORTHODONTIC BRACKET WITH ALIGNMENT AND INDENTIFICATION MARKING

BACKGROUND OF THE INVENTION

1. Field of the Invention

This invention relates to translucent or transparent orthodontic brackets that are marked with removable structure to facilitate identification of the brackets and positioning of the brackets during bonding.

2. Description of the Related Art

Orthodontic treatment involves movement of malpositioned teeth to orthodontically correct locations. During some types of orthodontic treatment, small, slotted devices known as brackets are bonded to the patient's teeth, and an archwire is placed in the slots of the brackets. The archwire serves as a track to guide movement of the teeth to desired positions.

In accordance with certain types of orthodontic treatment techniques, the orthodontist may carefully align the archwire slot of the bracket with respect to certain reference axes of the oral cavity in order to facilitate guiding the tooth toward its desired location. For example, many orthodontists employ a technique known as the "straight-wire technique" wherein the archwire is intended to be straight and parallel to the desired occlusal plane during the final stages of treatment. In this technique, it is important that the archwire slots of the brackets are correctly aligned to reference axes of the tooth during bonding of the bracket to the tooth so that the archwire is straight and unbent when the teeth are finished moving to their desired, respective locations.

In recent years, there has been increased interest in orthodontic brackets that are made of a material that transmits light, since such brackets are much less noticeable to the casual observer and are hence considered more aesthetic than, for example, brackets made of a metallic material. Advantageously, the color of the underlying tooth is often visible through such light transmissive brackets, enabling the brackets to take on the color of the tooth and blend with adjacent tooth structure.

Light-transmissive orthodontic brackets are often made of plastic or ceramic materials, and can be translucent or transparent. Examples of translucent ceramic brackets are described in U.S. Pat. No. 4,954,080, which is assigned to the assignee of the present invention. Examples of brackets made of plastic material are described in U.S. Pat. No. 5,318,440, which is also assigned to the assignee of the present invention.

However, it can also be appreciated that brackets that are translucent or transparent are more difficult to see in the oral cavity by the orthodontist when the brackets are bonded to teeth, such that alignment of the bracket with respect to the occlusal plane of the patient is also rendered more difficult. Moreover, some orthodontists prefer relatively small brackets, which are more difficult to see and align with the occlusal plane in comparison to larger brackets.

Some manufacturers have provided a removable positioning jig with each bracket to assist in aligning the bracket to the tooth. For example, the assignee of the present invention has provided removable long axis indicators with its "TRANSCEND" brand brackets, and such indicators include one leg for alignment with the long axis of the tooth, and a second, transverse leg for alignment with the occlusal plane. The jigs are color-coded to help identify the tooth for which the bracket is intended. While such indicators are deemed satisfactory by many orthodontists, each indicator must be carefully removed from the bracket after bonding and disposed of before the archwire can be installed.

Other attempts have also been made to enhance the visibility of light-transmissive brackets during bonding. U.S. Pat. No. 4,952,141 discloses a bracket having an adhesive strip, a paint strip or an elastomeric material removably received in the archwire slot. However, such a marking is difficult to see if, for example, a dental probe or other tool is placed in the slot during final positioning of the bracket.

U.S. Pat. No. 5,074,783 describes a bracket having a removable water-soluble ink on its outer, labial surface. Unfortunately, the ink may rub off during shipping or handling of the bracket before the bracket is bonded to the tooth. The ink also renders the bracket somewhat unattractive until such time as the bracket is bonded in place and the ink is removed, such that a patient looking at a set of new, unused brackets might be dissuaded from their selection and use.

SUMMARY OF THE INVENTION

The present invention is directed toward an orthodontic bracket made of a material that transmits light, and comprises a base and a body connected to the base. The body has an elongated archwire slot for receiving an archwire. The bracket includes at least one occlusal tiewing extending in an occlusal direction from the body, and at least one gingival tiewing extending in a gingival direction from the body. An occlusal ligature channel is located lingually adjacent each occlusal tiewing, and a gingival ligature channel is located lingually adjacent each gingival tiewing. A removable colorant is received in at least one of the ligature channels. The colorant extends in a direction generally parallel to the longitudinal axis of the archwire slot and is visible through the adjacent tiewing for facilitating positioning of the bracket on a tooth.

The present invention is advantageous in that the removable colorant is at least partially protected by the overlying, adjacent tiewing. As such, the colorant is less likely to be wholly or partially removed by rubbing or otherwise contacting the structure during manufacture, during initial handling of the bracket by the orthodontist and during placement of the bracket on the tooth. Locating the colorant beneath the tiewings also does not detract from the appearance of the bracket, and is therefore more aesthetically appealing to the patient in comparison to brackets known in the prior art.

The present invention is also directed toward an orthodontic marking system that comprises an orthodontic set-up tray having a number of receptacles and a number of markers adjacent at least some of the receptacles. At least one of the markers identifies a first color and at least one other of the markers identifies a second color that is different than said first color. The orthodontic marking system also includes a number of orthodontic brackets each received in a corresponding receptacle of the set-up tray. At least one of the brackets includes a removable structure having a third color, and at least one other of the brackets includes a removable structure having a fourth color that is different than the third color. The third color is visibly the same as the first color and the fourth color is visibly the same as the second color, whereby the receptacles are color-coded to receive the brackets.

DETAILED DESCRIPTION OF THE PREFERRED EMBODIMENTS

Figure 1:
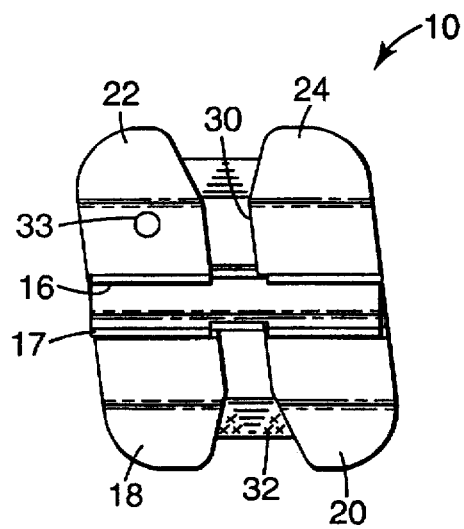
FIG. 1 is a front elevational view of an orthodontic bracket constructed in accordance with one embodiment of FIG. 2 is a side elevational view of the orthodontic bracket illustrated in FIG. 1, taken in a direction looking toward its mesial side.
Figure 2:
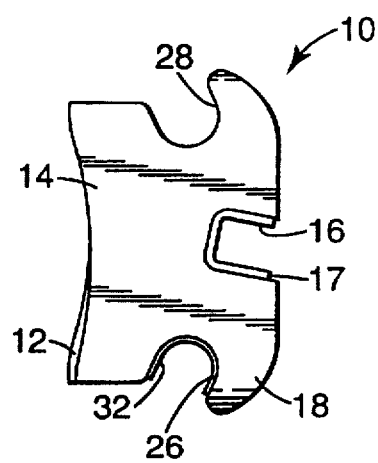
Figure 3:
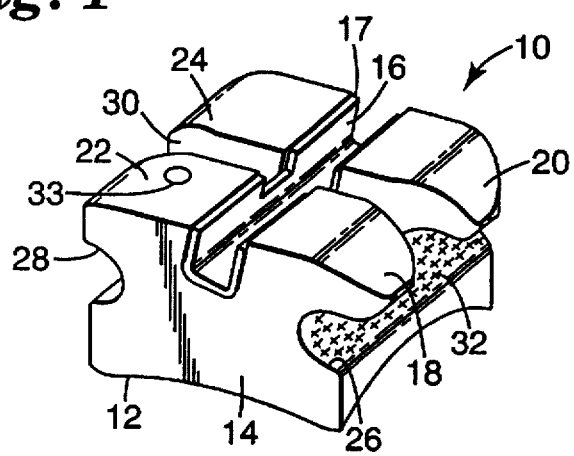
FIG. 3 is a perspective view of the orthodontic bracket shown in FIG. 1 and 2, taken in a direction looking toward its mesial, occlusal and bucco-lingual sides.

An orthodontic bracket 10 constructed in accordance with the principles of the present invention is illustrated in detail in FIGS. 1–3. The bracket 10 is made of a light-transmissive material that is translucent or transparent to the passage of light in the visible wave lengths. The color of the underlying tooth is visible through the bracket 10 and the bracket 10 thereby presents an aesthetically pleasing appearance. The material of the bracket 10 may be a polymer, a monocrystalline or polycrystalline ceramic, or other material that transmits light in either a direct or diffuse manner.

Suitable examples of ceramic materials include monocrystalline alumina such as is described in U.S. Pat. No. 4,639,218, and polycrystalline alumina such as is described in U.S. Pat. No. 4,954,080 which is incorporated by reference herein. Suitable polymeric materials are set out in U.S. Pat. No. 5,318,440 which is incorporated by reference herein. If the bracket 10 is made of a polymeric material, the bracket 10 may include reinforcing fibers such as is described in U.S. Pat. No. 5,318,440.

The bracket 10 includes a base 12 for bonding the bracket 10 to a tooth surface. The base 12 has a concave, compoundly-curved configuration that matches the convex configuration of the external surface of the particular tooth for which it is intended. A suitable light-curable adhesive for fixing the bracket 10 to a tooth is described in U.S. Pat. No. 5,354,199.

The bracket 10 includes a body 14 that extends outwardly from the base 12 in a buccal-labial direction (i.e., in a direction toward the cheeks or lips of the patient when the bracket 10 is in place in the oral cavity). The body 14 includes an elongated archwire slot 16 that has a generally rectangular configuration in transverse cross-section. In accordance with a treatment technique preferred by many orthodontists, the archwire slot 16 extends in a direction that is parallel to the occlusal plane of the patient when the underlying tooth is in its desired position for correct occlusion.

Optionally, and as shown in FIGS. 1–3, a metallic archwire slot liner 17 is fixed to the bracket body 14 and has an inner channel presenting the archwire slot 16. The archwire slot liner 17 enhances sliding mechanics of the bracket 10 along an archwire during orthodontic therapy, and also enhances strength of the bracket 10. Examples of suitable archwire slot liners are described in U.S. Pat. Nos. 5,380,196 and 5,358,402, which are incorporated by reference herein.

Two spaced apart tiewings 18, 20 are integrally connected to the body 14 and extend away from the body 14 in a occlusal direction (i.e., in a direction toward the outer end of the underlying tooth). Two other spaced apart tiewings 22, 24 are also integrally connected to the body 14 and extend outwardly from the body 14 in a gingival direction (i.e., in a direction toward the adjacent gingival tissue). The tiewings 18, 22 are located on a distal portion of the bracket 10 (i.e., on a portion of the bracket 10 facing away from the middle of the patient's dental arch). The tiewings 20, 24 are located on a mesial portion of the bracket 10 (i.e., on a portion of the bracket 10 toward from the middle of the dental arch).

An occlusal ligature channel 26 is located lingually (i.e., in a direction toward the patient's tongue) of each of the occlusal tiewings 18, 20. Similarly, a gingival ligature channel 28 is located lingually of each gingival tiewing 22, 24. The ligature channels 26, 28 are similar to ligature channels commonly found in orthodontic brackets for receiving a wire ligature or an elastomeric ligature. The ligatures extend around the archwire and along the channels 26, 28 for retaining the archwire in the archwire slot 16.

As can be appreciated by reference to FIGS. 2 and 3, each of the elongated channels 26, 28 has a general shape resembling a half-cylinder when viewed in a direction transverse to its longitudinal axis. The side of the channels 26, 28 nearest the base 12 presents a continuous surface, while the opposite side of the channels 26, 28 next to the respective tiewings presents two surfaces that are separated by the space between adjacent pair of tiewings. The side of each channel 26, 28 nearest the archwire slot 16 is partially interrupted by a narrowed "vertical" slot 30 that extends in an occlusal-gingival direction between the occlusal tiewings 18, 20 and also between the gingival tiewings 22, 24.

A removable structure or colorant 32 is received in at least one of the ligature channels 26, 28 for facilitating alignment of the bracket 10 to the occlusal plane or to some other reference plane or axis. In the embodiment shown in the drawings, the colorant 32 is placed only in the occlusal ligature channel 26, and substantially covers the entire surface of the channel 26 along its length and on its lingual, gingival and buccal-labial surfaces. Alternatively, however, the colorant 32 may be placed only in the gingival ligature channel 28, or in both of the ligature channels 26, 28.

As used herein, a colorant means a paint, dye, ink, stain or other type of coloring agent that is applied as a liquid to one or both of the ligature channel 26, 28. The colorant 32 may also be a gelatin coating or a layer of thin paper that dissolves upon exposure to water. Preferably, the colorant 32 is a water-based, non-toxic layer of non-opaque paint. The colorant 32 is applied by a brush, sponge or blotter that is moved along the length of the ligature channel 26. As an alternative, a number of brackets similar to bracket 10 may be aligned in a row, and a string-like material such as dental floss that has been wetted with the colorant 32 is moved through all of the occlusal ligature channels simultaneously.

The colorant 32 is visible when looking toward the labial face of the bracket 10 and through the light-transmissive material of the occlusal tiewings 18, 20. The elongated shape of the layer of colorant 32 thus aids the orthodontist in aligning the bracket 10 to the occlusal plane of the patient. The appearance of the colorant 32 is somewhat diffused when the bracket 10 is made of a translucent material and thus presents an aesthetically pleasing appearance even though the colorant 32 is sufficiently dark for ease of viewing. Preferably, the colorant 32 is not entirely opaque, so that a portion of the light present in the occlusal ligature channel 26 passes through the colorant 32 and through the occlusal tiewings 18, 20 to further enhance viewing of the bracket 10 and alignment of the latter.

Once the bracket 10 is properly positioned on the tooth, the adhesive is allowed to cure in order to securely fix the bracket 10 to the tooth. For example, if the adhesive is a light curable adhesive, light is directed from a light curing unit toward the adhesive adjacent the bracket base 12 to initiate the photopolymerization reaction. The passage of the light to the adhesive is not significantly hindered by the presence of the colorant 32 since the colorant 32 is preferably located in only one of the ligature channels, and is preferably not opaque to the passage of light from the light curing unit.

Once the bracket 10 is fixed to the tooth, the colorant 32 is removed by directing a spray or rinse of water toward the occlusal ligature channel 26. Preferably, the colorant 32 is removed without rubbing or without application of chemical rinses such as ethanol.

Optionally, the bracket 10 has a locator mark 33 that is preferably placed on the distal-gingival tiewing 24. The locator mark 33 helps insure that the bracket 10 is the proper bracket for the selected tooth to which it is to be bonded, and also serves to help insure that the bracket 10 is properly oriented when placed on the selected tooth. The locator mark 33 may be made by forming a dimple (or alternatively an integral, protruding surface) on the buccal-labial face of the distal gingival tiewing 22. As another option, the locator mark 33 includes a removable label or a colorant (such as a paint, dye, ink, stain or other type of coloring agent) in the shape of a round dot or other configuration on the buccal-labial face of the distal gingival tiewing 24, and may be used in combination with the dimple or protruding surface described in the preceding sentence. If a colorant is used, the colorant is non-toxic and preferably water-based so that it readily rinses away when subjected to a spray of water or water rinse, preferably at the same time that the colorant 32,is removed.

As another alternative, the locator mark 33 is made of a colored, water-soluble adhesive (such as an indirect bonding adhesive, no. 704-050, from 3M Unitek). Such an adhesive has been found to remain affixed to a cleaned surface of the distal-gingival tiewing 24 with substantial tenacity, even when a number of brackets made of a relatively hard material such as ceramic are placed together in bulk in a bag. Another advantage of such adhesive is that the adhesive readily dries in a few minutes under normal ambient conditions after application to the bracket without the use of a drying oven or the like. Yet, the water-based adhesive of the locator mark 33 is easily removed by a water rinse or spray after bonding of the brackets has been completed. By comparison, the paint or ink markings used on some prior art ceramic brackets have been known to partially or even completely disappear after a period of time when such brackets are subjected to contact with each other in a bag.

Figure 4:
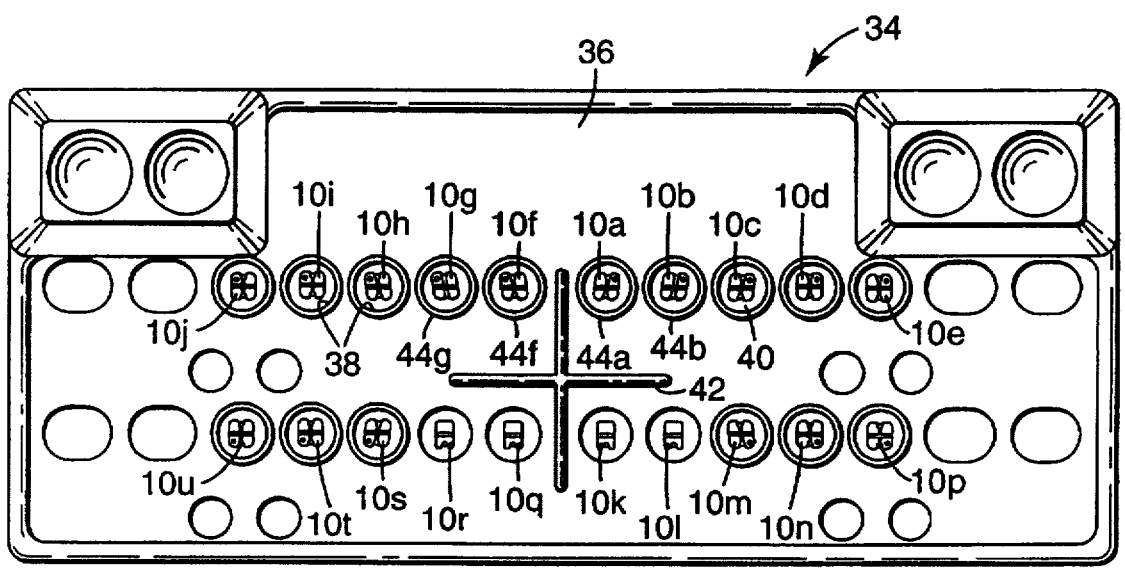
FIG. 4 is a reduced view of another embodiment of the invention that includes an orthodontic set-up tray containing a number of orthodontic brackets constructed similar to the bracket that is shown in FIGS. 1–3.

FIG. 4 is an illustration of a patient set-up tray 34 of the type commonly used in orthodontic offices. A preferred set-up tray is catalog no. 709-019, from 3M Unitek Corporation, and has a substrate 36 with a number of openings or receptacles 38 arranged in a pattern that corresponds to respective teeth in the patient's oral cavity. An adhesive coated film 40 extends along the bottom of the substrate 36, and is exposed in areas beneath the receptacles 38 in order to releasably hold orthodontic brackets in place as the desired brackets are selected and carried to the patient in the operatory.

Orthodontic brackets 10a–10u are arranged on the set-up tray 34 in certain receptacles 38 that correspond to particular teeth. Each bracket 10a–10u is somewhat similar to bracket 10 described above, in that each bracket 10a–10u has a removable colorant located in its occlusal ligature channel. A raised cross-shaped indicia 42 formed in the substrate 36 provides a reference point which signifies the midpoint of the patient's upper and lower dental arch.

Viewing FIG. 4, the horizontal row of seven receptacles 38 on the upper right-hand side of the center of the indicia 42 corresponds to the row of teeth on the left-hand side of the patient's upper arch. The row of receptacles 38 to the upper left-hand side of the center of the indicia 42 corresponds to the row of teeth on the right-hand side of the patient's upper dental arch. Similarly, the two rows of receptacles 38 located to the lower right-hand side of the center of the indicia 42 and the lower left-hand side of the center of the indicia 42 correspond to teeth on the left-hand and right-hand side of the patient's lower arch respectively.

In FIG. 4, the brackets designated 10a–10e each have a shape that is adapted for use with corresponding tooth on the left-hand side of the patient's upper arch. Bracket 10a is for use with an upper left central incisor tooth, 10b for an upper left incisor lateral tooth, 10c for an upper left cuspid tooth, 10d for an upper left first bicuspid tooth and 10e for an upper left second bicuspid tooth. The brackets 10f–10j are for use with teeth on the patient's upper right dental arch quadrant. Bracket 10f is adapted for use with an upper right central incisor tooth, 10g for an upper right first lateral tooth, 10h for an upper right cuspid tooth, 10i for an upper right first bicuspid tooth and 10j for an upper right second bicuspid tooth.

The brackets 10k–10p are configured for use with respective teeth in the patient's lower left dental arch quadrant. Bracket 10k is constructed for use with the lower left central incisor tooth, 10l for the lower left lateral incisor tooth, 10m for the lower left cuspid tooth, 10n for the lower left first bicuspid tooth and 10p for the lower left second bicuspid tooth. The brackets 10q–10u are adapted for use with corresponding teeth in the patient's lower right dental arch quadrant. Bracket 10q is for a lower right central incisor tooth, 10r for a lower right lateral incisor tooth, 10s for a lower right cuspid tooth, 10t for a lower right first bicuspid tooth and 10u for a lower right second bicuspid tooth.

The set-up tray 34 includes a number of markers 44 that are located adjacent at least some of the receptacles 38. Preferably, the markers 44 are provided in a variety of colors that visibly different when viewed by the naked eye. For example, markers 44a and 44f may have a blue color, while markers 44b and 44g may have a pink color.

The markers 44 shown in FIG. 4 are an annular-shaped section of colored label stock having a pressure sensitive adhesive for bonding with the substrate 36. Each marker 44 surrounds a corresponding receptacle 38, although other shapes are, of course, possible. For example, the markers 44 may be solid circles of label stock that are placed above or below corresponding receptacles. Alternatively, the markers 44 may be placed on the film 40 and be visible through the receptacles 38, and also carry an adhesive for releasably securing the brackets 10a–10u to the set-up tray 34. As another option, the markers 44 may simply identify the colors by printing the word describing the color directly on the tray 34 or on a label applied to the tray.

Advantageously, brackets 10a–10u are color-coded to the markers 44 to facilitate initial identification of the brackets, to aid in placing the brackets in proper locations on the set-up tray 34, and to facilitate placing the brackets 10a–10u on proper teeth in the oral cavity. More particularly, the colorant 32 for brackets 10a and 10f has a blue color that matches the blue color of markers 44a and 44f. Similarly, the colorants of the brackets 10b and 10g have a red color that matches the red color of markers 44b and 44g.

In the example described above, brackets 10c and 10h have a colorant with a green color, brackets 10d, 10e, 10i and 10j have a colorant having a yellow color, brackets 10k, 10l, 10q and 10r have no colorant, brackets 10m and 10s have a colorant with a purple color, brackets 10n and 10t have a colorant with an orange color and brackets 10p and 10u have a colorant with a black color. As such, eight different colors for the colorant 32 are used when twenty brackets, or five brackets in each of the arch quadrants, are employed. The upper bicuspid brackets (i.e., brackets 10d, 10e, 10i and 10j) may have a colorant of the same color, and the lower anterior brackets (i.e., lower central and lateral incisor brackets 10k, 10l, 10q and 10r) may have a colorant of the same color (or, as illustrated, lack a colorant) since the brackets within each group are essentially the same.

Other variations are also possible. For example, each of the brackets for use with the upper left quadrant (i.e., brackets 10a–10e) may have a colorant 32 of the same color, while the brackets for use with the patient's upper right quadrant (i.e., brackets 10f–10j) have a colorant 32 of another color that is different than the color of the colorant 32 for the brackets 10a–10e. Likewise, the lower left quadrant brackets 10k–10p have a colorant with a third color, while the lower right quadrant brackets 10q–10u have a colorant with a fourth color. In such an instance, the markers 44 would also have a color to correspond to the color of the brackets to be located in the adjacent receptacles 38.

As used herein, a colorant having a color that is different than the color of another colorant means that the value of $\Delta_{E_{ab}}*$ in the CIE 1976 L*a*b* ("CIELAB") color difference equation $\Delta_{E_{ab}}* = (\Delta L*^2 + \Delta a*^2 + \Delta b*^2)^{1/2}$ is greater than about 3, wherein $L* = 116(Y/Y_n)^{1/3} - 16$, $a* = 500[(X/X_n)^{1/3} - (Y/Y_n)^{1/3}]$, $b* = 200[(Y/Y_n)^{1/3} - (Z/Z_n)^{1/3}]$, and wherein $X_n$, $Y_n$, and $Z_n$ are the tristimulus values of the reference white.

Conversely, the colors are the same when the value of $\Delta_{E_{ab}}*$ is less than or equal to about 3. Additional information regarding the CIELAB equation is set out in Billmeyer & Saltzman, *Principles of Color Technology* (Interscience Publishers, N.Y., copyright 1981) p. 103. Color measurements may be taken using, for example, a Hunter Lab Scan 6000 Spectrocolorimeter instrument. When $\Delta_{E_{ab}}*$ is greater than about 3, the colors are generally considered visibly different to the naked eye of the ordinary observer (i.e., an ordinary individual who is not an orthodontist or dentist) without the use of instrumentation. The use of a color coded marking system as provided by the colorant 32 and the markers 44 is advantageous as opposed to other marking systems involving symbols of different shapes, as construction of a symbol having a particular shape on each bracket 10 is unnecessary, and in any case may be difficult to see by the unaided eye. Moreover, the colorant 32 may be easily removed after bonding of all the brackets 10 has been completed so that the aesthetic appearance of the brackets 10 is not diminished.

The locator mark 33 (not designated by numerals in FIG. 4) serves to differentiate for example the bracket 10a from the bracket 10f so that the likelihood of inadvertent bracket selection is further reduced. If desired, the locator mark 33 may be a colorant having a color similar to the color of the colorant 32 for the particular bracket, or may be a different color such that each bracket has a locator mark 33 with identical colors.

As another alternative, the colorant of each bracket may match a color provided on a package containing the bracket. For example, individual packages each containing a single adhesive precoated bracket, such as the packages described in U.S. Pat. Nos. 5,348,154 and 5,350,059, could be provided with a cover or lid having a colored strip, marker or other structure that matches the colorant of the bracket contained in the package. In such an instance, a set-up tray having a number of holes or receptacles to receive the packages would also be provided with a colored strip, marker or other structure adjacent each receptacle to identify which package, and consequently which bracket, should be received in that particular receptacle. As a result, both the package and the contained bracket would be color-coded to match certain receptacles and the package need not be opened until such time as the bracket is to be placed on the tooth.

While the foregoing description has been set out in detail according to our presently preferred embodiments of the invention, it will be understood by those skilled in the art that other modifications, additions and improvements may be added without departing from the spirit of our invention. Accordingly, the scope of the invention should be limited only by a fair reading of the claims that follow and their equivalents.

We claim:

1. An orthodontic bracket made of a material that transmits light, said bracket comprising:

a base;

a body connected to said base and having an elongated archwire slot for receiving an archwire;

at least one occlusal tiewing extending in an occlusal direction from said body;

at least one gingival tiewing extending in a gingival direction from said body;

an occlusal ligature channel located lingually adjacent each occlusal tiewing;

a gingival ligature channel located lingually adjacent each gingival tiewing; and a colorant received in at least one of said ligature channels, said colorant extending in a direction generally parallel to the longitudinal axis of said archwire slot and visible through the adjacent tiewing for facilitating positioning of said brackets on a tooth.

2. The orthodontic bracket of claim 1, wherein said colorant is received in said occlusal ligature channel.

3. The orthodontic bracket of claim 1, wherein said colorant is selected from the group consisting of a paint, a dye, a stain or an ink.

4. The orthodontic bracket of claim 3, wherein said colorant is water-based.

5. The orthodontic bracket of claim 1, and including a locator mark on at least one of said tiewings.

6. The orthodontic bracket of claim 5, wherein said at least one gingival tiewing includes a mesial gingival tiewing and a distal gingival tiewing, and wherein said locator mark is located on said distal gingival tiewing.

7. The orthodontic bracket of claim 1, wherein said removable structure is received in said occlusal channel, and wherein said at least one occlusal tiewing comprises a mesial tiewing and a distal tiewing that is spaced from said mesial tiewing.

8. The orthodontic bracket of claim 1, wherein said colorant is non-opaque.

9. The orthodontic bracket of claim 1; and including a set-up tray having a number of receptacles and a number of markers adjacent at least some of the receptacles, wherein said colorant and at least one of said markers have the same color.

10. An orthodontic marking system comprising:

an orthodontic set-up tray having a number of receptacles arranged in a pattern corresponding to teeth of an oral cavity, said set-up tray including a number of markers adjacent at least some of said receptacles, at least one of said markers identifying a first color and at least one other of said markers identifying a second color that is different than said first color; and a number of orthodontic brackets, said receptacles each receiving a single one of said brackets, at least one of said brackets including removable structure having a third color, at least one other of said brackets including removable structure having a fourth color that is different than said third color, said third color being visibly the same as said first color and said fourth color being visibly the same as said second color, whereby said receptacles are color-coded to receive said brackets, and wherein said removable structure comprises a colorant.

11. The orthodontic marking system of claim 10, wherein said markers surround the corresponding receptacles.

12. The orthodontic marking system of claim 10, wherein said markers comprise a section of label stock.

13. The orthodontic marking system of claim 10, wherein each marker is located to one side of the corresponding receptacle.

14. The orthodontic marking system of claim 10, wherein said brackets each include at least one tiewing and a ligature channel located lingually adjacent said at least one tiewing, and wherein said removable structure is received in said ligature channel and is visible through each adjacent tiewing.

* * * * *